US006908773B2

United States Patent
Li et al.

(10) Patent No.: US 6,908,773 B2
(45) Date of Patent: Jun. 21, 2005

(54) ATR-FTIR METAL SURFACE CLEANLINESS MONITORING

(75) Inventors: Lain-Jong Li, HsinChu (TW);
Syun-Ming Jang, Hsin-Chu (TW);
Chung-Chi Ko, Nantou (TW)

(73) Assignee: Taiwan Semiconductor Manufacturing Co., Ltd., Hsin Chu (TW)

( * ) Notice: Subject to any disclaimer, the term of this patent is extended or adjusted under 35 U.S.C. 154(b) by 370 days.

(21) Appl. No.: 10/102,574

(22) Filed: Mar. 19, 2002

(65) Prior Publication Data

US 2003/0179368 A1 Sep. 25, 2003

(51) Int. Cl.[7] .......................... G01R 31/26; H01L 21/66
(52) U.S. Cl. ........................ 438/14; 438/16; 356/237.2; 356/369
(58) Field of Search ........................... 438/14, 16, 250, 438/324; 356/237.2, 369, 238.3

(56) References Cited

U.S. PATENT DOCUMENTS

| 5,160,826 | A | * | 11/1992 | Cohen et al. ........... 250/339.08 |
| 5,905,269 | A | * | 5/1999 | Venkataramani et al. ... 250/504 R |
| 6,141,100 | A | * | 10/2000 | Burka et al. ............. 356/451 |
| 6,433,877 | B2 | * | 8/2002 | Watanabe et al. ........... 359/600 |
| 6,774,368 | B2 | * | 8/2004 | Busch et al. ............ 250/339.09 |
| 6,784,428 | B2 | * | 8/2004 | Rabolt et al. .......... 250/339.02 |
| 2002/0180991 | A1 | * | 12/2002 | Takoudis et al. |
| 2004/0113077 | A1 | * | 6/2004 | Franzen et al. .......... 250/338.1 |
| 2004/0195511 | A1 | * | 10/2004 | Elmore et al. ......... 250/339.02 |

OTHER PUBLICATIONS

UK Patent Application (0013800) Watanabe et al. (Apr. 10, 2000).*

* cited by examiner

*Primary Examiner*—W. David Coleman
*Assistant Examiner*—Khiem Nguyen
(74) *Attorney, Agent, or Firm*—Tung & Associates

(57) ABSTRACT

Attenuated total reflectance (ATR)-Fourier transform infrared (FTIR) metal surface cleanliness monitoring is disclosed. A metal surface of a semiconductor die is impinged with an infrared (IR) beam, such as can be accomplished by using an ATR technique. The IR beam as reflected by the metal surface is measured. For instance, an interferogram of the reflected IR beam may be measured. A Fourier transform of the interferogram may also be performed, in accordance with an FTIR technique. To determine whether the metal surface is contaminated, the IR beam as reflected is compared to a reference sample. For example, the Fourier transform of the interferogram may be compared to the reference sample. If there is deviation by more than a threshold, the metal surface may be concluded as being contaminated.

10 Claims, 2 Drawing Sheets

ATR-FTIR METAL SURFACE CLEANLINESS MONITORING

FIELD OF THE INVENTION

This invention relates generally to metal surfaces of semiconductor devices, such as bonding pads, and more particularly to monitoring the cleanliness of such metal surfaces.

BACKGROUND OF THE INVENTION

Once semiconductor devices on semiconductor wafers have been fabricated, they must be packaged in order to actually be used. The individual dies on the wafers are separated from one another, and then are typically put in a protective package. They may also be mounted onto the surface of a ceramic substrate as part of a hybrid circuit, put into a large package with other chips as part of a multi-chip module (MCM), or be connected directly on board a printed circuit or chip-on-board (COB). However, packaging the wafers individually into protective packages is still the most common back-end process.

FIG. 1 shows an example of a partially exposed packaged chip 100. The packaged chip 100 includes a die-attachment area 102. This is typically located in the center of the packaged chip 100, and is where the chip 114, or die, is securely attached into the package. The die-attachment area 102 may have an electrical connection that services to connect the back of the chip 114 to the rest of the lead system.

The packaged chip 100 also includes a metal lead system. The system inner connections are referred to as inner leads, such as the inner lead 108, bonding lead tips, or bond fingers. The inner leads are generally the narrowest portions of the lead system. The leads become progressively wider, ending outside the package. These portions of the lead system are called outer leads, such as the outer lead 106.

The lead system is connected to the chip 114 usually via bonding wires, such as the bonding wire 104 connecting to bonding pads of the chip 114, such as the bonding pad 112. Besides bonding wires, bonding balls and other types of electrical connections can be used. The entire chip 114 is enclosed in an enclosure 110. The enclosure 110 provides protection and heat-dissipation functions, and may be hermetically or non-hermetically sealed.

For the bonding wires or other types of electrical connections to successfully bond to the bonding pads of the chip, which can be generally defined as the (metal) electrical terminals on the chip used for connection to the package electrical system, the bonding pads must be free from contamination. Poor bonding pad surface cleanliness can result in pad delamination, as well as electrical connection pull or shear failure. This can reduce packaged chip yield, and/or cause failure once the package chip has been deployed into the field, such as being sold to a customer, and so on.

Bonding pad cleanliness has traditionally been tested by x-ray photoelectron spectroscopy (XPS), which is a technique for studying semiconductor surfaces. In XPS, a beam of x-rays is incident on the semiconductor surface. The x-rays transfer their energy to electrons in the semiconductor, which enables the electrons to escape from the surface. Measuring the energy of the escaped electrons allows a determination of the chemical identity of the atoms from which they came. This energy can be correlated to whether the electrons came from contamination, from the metal of the bonding pad itself, and so on.

However, XPS has a number of disadvantages when used for determining metal surface cleanliness, such as bonding pad surface cleanliness. It cannot be used as an in-line monitoring technique to monitor all or substantially all of the bonding pads of semiconductor dies. This is because XPS is a destructive process, and ends up destroying the bonding pad that it is examining. Therefore, XPS can only be performed on a sample basis, and not on all the chips that are to be packaged.

Furthermore, XPS requires a relatively large minimum testing area, such as 200 micron by 200 micron. However, as chips have become progressively smaller, their bonding pads are also becoming progressively smaller, and it is anticipated that bonding pads as small as 80 micron by 80 micron may become commonplace. As a result, XPS cannot be used to monitor such small bonding pads, since the sizes of these pads are less than the minimum area required by XPS.

Therefore, there is a need for a metal surface cleanliness monitoring technique that overcomes these disadvantages. Specifically, such a monitoring technique should not be a destructive process, so that in-line monitoring can be performed. The monitoring technique should also be able to be performed relative to a small minimum testing area, such as 80 micron by 80 micron. For these and other reasons, there is a need for the present invention.

SUMMARY OF THE INVENTION

The invention relates to attenuated total reflectance (ATR)-Fourier transform infrared (FTIR) metal surface cleanliness monitoring. A metal surface of a semiconductor die is impinged with an infrared (IR) beam, such as can be accomplished by using an ATR technique. The IR beam as reflected by the metal surface is measured. For instance, an interferogram of the reflected IR beam may be measured. A Fourier transform of the interferogram may also be performed, in accordance with an FTIR technique. To determine whether the metal surface is contaminated, the IR beam as reflected is compared to a reference sample. For example, the Fourier transform of the interferogram may be compared to the reference sample. If there is deviation by more than a threshold, the metal surface may be concluded as being contaminated.

Embodiments of the invention provide for advantages over the prior art. The ATR-FTIR metal surface cleanliness monitoring of the invention is non-destructive, so it can be used as an in-line process to test all or substantially all of the metal surfaces of a number of dies of a number of semiconductor wafers. Furthermore, the process is relatively fast, ensuring a high throughput, and is highly sensitive. The minimum area required for testing can be as small as 25 micron by 25 micron, such that even small metal surfaces, such as small bonding pads, of semiconductor dies can be tested. Other advantages, aspects, and embodiments of the invention will become apparent by reading the detailed description that follows, and by referring to the accompanying drawings.

DETAILED DESCRIPTION OF THE INVENTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims. For instance, whereas the invention is substantially described in relation to a bonding pad, it is applicable to other metal surfaces of semiconductor dies of semiconductor wafers as well, such as metal trenches, and so on.

Figure 1:
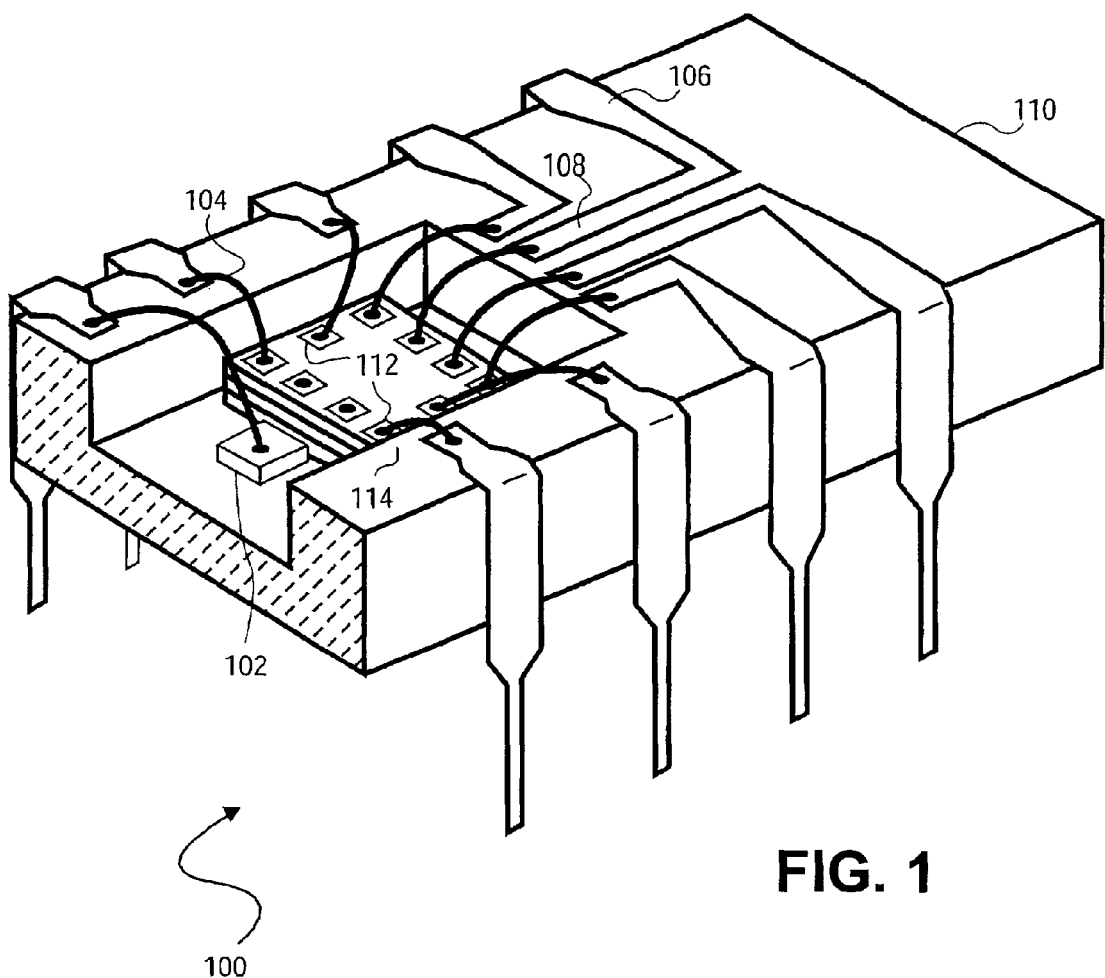
FIG. 1 is a diagram of a partially exposed packaged semiconductor die in which the die has bonding pads that are connected to external metal leads for electrical connection of the die. Embodiments of the invention may be implemented in conjunction with the bonding pads of the die of FIG. 1, as an example.
Figure 2:
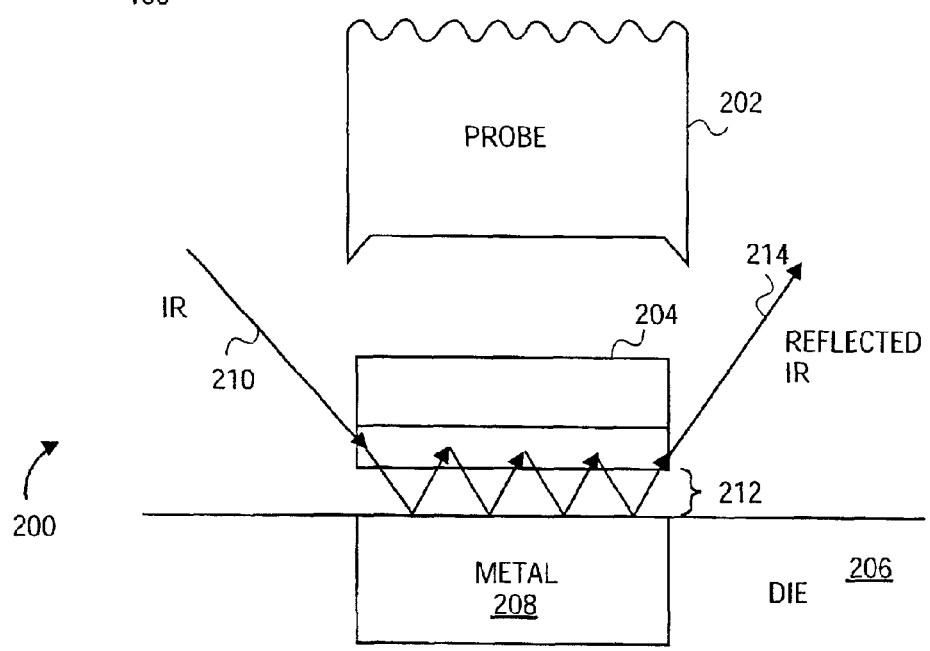
FIG. 2 is a diagram of a system according to an embodiment of the invention that specifically shows how an infrared (IR) beam impinges on a metal surface and is then reflected, where the reflected IR beam can be used to determine whether the metal surface is contaminated.

FIG. 2 shows a system 200 according to an embodiment of the invention. The system 200 includes an infrared (IR) probe 202 that has a clear lens 204, such as a quartz lens. The IR probe 202 is positioned over a semiconductor die 206 that has a metal surface 208, such as a bonding pad, a metal trench, and so on. The metal may be copper, gold, aluminum, or another metal. An IR beam 210 is incident to and impinges the metal surface 208, by the IR probe 202, such that reflections 212 take place between the metal surface 208 and the lens 208. Ultimately, a reflected IR beam 214 results, which is detected by a sensor not shown in FIG. 2, but which may be part of the IR probe 202. Although not particularly shown in FIG. 2, the lens 204 may be in direct physical contact with the metal surface 208.

The IR beam 210 may impinge the metal surface 208, resulting in the IR reflections 212 and ultimately the reflected IR beam 214, in accordance with an attenuated total reflectance (ATR) technique, such that the IR probe 202 is an ATR IR probe. ATR is a reflectance sampling technique in which infrared radiation impinges on a prism of infrared transparent material of high refractive index. Because of the internal reflectance, the light reflects off the crystal surface at least once before leaving it. The infrared radiation sets up an evanescent wave that extends beyond the surface of the crystal, and into the sample that is in contact with the crystal. Thus, in the case of the system 200 of FIG. 2, the crystal is the lens 204, and the sample is the metal surface 208. The evanescent wave includes the IR reflections 212.

The reflected IR beam 214 can be measured as an interferogram. An interferogram is a plot of IR detector or sensor response, where the IR detector or sensor is not shown in FIG. 2, or may be part of the probe 202, versus optical path difference. Such an interferogram can then be Fourier transformed, to turn the interferogram into an infrared spectrum. In other words, Fourier transform IR (FTIR) spectroscopy of the reflected IR beam 214 can be performed. FTIR is a method of obtaining infrared spectra by first measuring the interferogram of the sample, such as the metal surface 208, by an interferometer or other device, such as the probe 202, and then performing a Fourier transform on the interferogram to obtain the spectrum.

The resulting reflected IR beam 214, as may be indicated by an interferogram or a Fourier transform of the interferogram, can then be compared with a reference sample of a known clean, non-contaminated metal surface. If there is deviation between the reflected IR beam 214 and the reference sample by more than a predetermined threshold, then it can be concluded that the metal surface 208 of FIG. 2 is contaminated. That is, the reference sample serves as a fingerprint identifying what the reflected IR beam 214, as indicated by an interferogram or a Fourier transform of the interferogram, of the metal surface 208 should substantially look like. If there is deviation from this fingerprint by more than a threshold that takes into account measurement tolerances, and so on, then it can be concluded that the metal surface 208 of FIG. 2 is contaminated. This is because such deviation results from the IR beam 210 being reflected by contaminants within or on the metal surface 208, and not just the metal surface 208 itself, resulting in a different reflected IR beam 214 unlike the reference sample.

Figure 3:
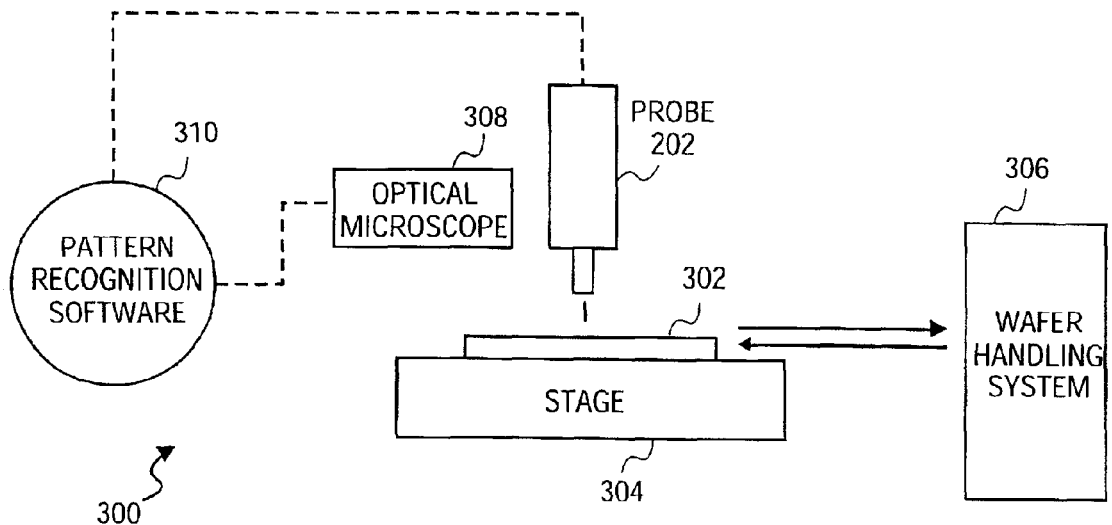
FIG. 3 is a diagram of a system according to an embodiment of the invention that is consistent with the system of FIG. 2, and shows on a more macro level a wafer positioned on a stage underneath an IR probe, so that pattern recognition software can be used to determine whether a metal wafer surface is clean or contaminated.

FIG. 3 shows a system 300 according to an embodiment of the invention. The system 300 is more macro in detail than the system 200 of FIG. 2, and the system 300 can subsume or incorporate the system 200. The system 300 includes a semiconductor wafer 302, the IR probe 202, a stage 304, a wafer handling system 306, an optical microscope 308, and pattern recognition software 310. The semiconductor wafer 302 is positioned on the stage 304. The semiconductor wafer 302 has a number of dies that have a number of metal surfaces, such as the die 206 of FIG. 2 that has the metal surface 208. The IR probe 202 is positionable over each metal surface of each semiconductor die of the semiconductor wafer 302, and is capable of measuring an IR beam incident to the metal surface as reflected by the metal surface, as has been described in conjunction with FIG. 2. That is, the IR probe 202 can be an ATR-IR probe, and so on.

The wafer handling system 306 allows the loading and unloading of semiconductor wafers, including the semiconductor wafer 302, and the transfer of the wafers to and from the stage 304. The optical microscope 308 is used to align the probe 202 over the semiconductor wafer 302, and for locating the individual dies of the wafer 302, and the metal surfaces of these dies. The probe 202 and the optical microscope 308 is preferably controlled by the pattern recognition software 310. Thus, the pattern recognition software 310 can be used to direct the probe 202 over each metal surface of each die of the semiconductor wafer 302 in turn, based on input from the optical microscope 308. The pattern recognition software 310 is more generally a pattern recognition component.

The pattern recognition software 310 also compares the reflected IR beam preferably detected by a detector or sensor of the probe 202 with a reference sample, as has been described. The software 310 may receive from the probe 202 an interferogram as representing the reflected IR beam, and may take a Fourier transform of the interferogram in accordance with FTIR analysis. The reflected IR beam, the interferogram, or the Fourier transform of the interferogram is compared by the software 310 with the reflected IR beam, the interferogram, or the Fourier transform of the interferogram of a reference sample.

Figure 4:
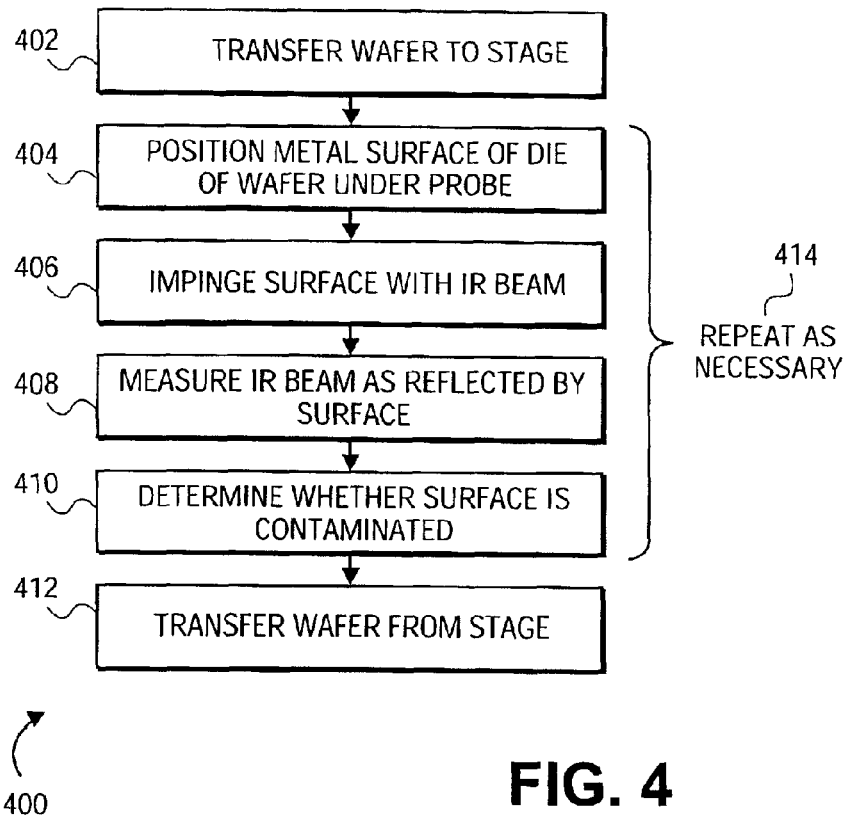
FIG. 4 is a flowchart of a method according to an embodiment of the invention for determining whether a metal surface of a die of a semiconductor wafer is contaminated, and which can be performed in conjunction with the system of FIG. 2 and/or the system of FIG. 3.

The reference sample is a known clean metal surface of the sample type of metal as the metal surfaces of the dies of the semiconductor wafer 302 are. Thus, the IR beam, the interferogram, or the Fourier transform of the interferogram of the reference sample (which may also be referred to as simply the reference sample for sake of convenience) represents what the input from the probe 202 should look like. Deviation by more than a predetermined threshold can thus lead the software 310 to conclude that the metal surface being examined is contaminated. FIG. 4 shows a method 400 according to an embodiment of the invention. The method 400 can be utilized in conjunction with the systems 200 and 300 of FIGS. 2 and 3, respectively, that have been described, such that description of the systems 200 and 300 is applicable to the method 400 as well. First, a semiconductor wafer is transferred onto a stage (402). A metal surface of a die of the semiconductor wafer is positioned under an IR probe (404), which impinges the metal surface with an IR beam (406). This may be consistent with and accomplished by employing an ATR technique, for instance. The IR beam as reflected by the metal surface is then measured (408), such as by the IR probe. The reflected IR beam may be measured as an interferogram of the metal surface.

Next, it is determined whether the metal surface is contaminated (410). Most generally, this involves comparing the reflected IR beam to a reference sample of what the reflected IR beam should look like if the metal surface were clean and free from contamination. If there is deviation by more than a predetermined threshold, then the metal surface is concluded to be contaminated. More specifically, the interferogram may have a Fourier transform performed thereon consistent with FTIR analysis, and the Fourier transform compared to a reference sample, such that deviation therefrom by more than a predetermined threshold leads to the conclusion that the surface is contaminated. The process of 404, 406, 408, and 410 may be repeated as necessary, as indicated by 414, such as for each metal surface of each die of the semiconductor wafer. Finally, the semiconductor wafer is transferred from the stage (412).

It is noted that, although specific embodiments have been illustrated and described herein, it will be appreciated by those of ordinary skill in the art that any arrangement is calculated to achieve the same purpose may be substituted for the specific embodiments shown. This application is intended to cover any adaptations or variations of the present invention. For example, whereas the invention is substantially described in relation to a bonding pad, it is applicable to other metal surfaces of semiconductor dies of semiconductor wafers as well, such as metal trenches, and so on. Therefore, it is manifestly intended that this invention be limited only by the claims and equivalents thereof.

What is claimed is:

1. A method comprising;
    impinging a metal surface of a semiconductor die with an infrared (IR) beam employing an attenuated total reflectance (ATR) technique;
    measuring the IR beam as reflected by the metal surface by measuring an interferogram of the metal surface, and performing a Fourier transform on the interferogram; and,
    determining whether the metal surface is contaminated based on the IR beam as reflected by the metal surface.

2. The method of claim 1, wherein determining whether the metal surface is contaminated based on the IR beam as reflected by the metal surface comprises comparing the Fourier transform of the interferogram to a reference sample and concluding that the metal surface is contaminated when the Fourier transform of the interferogram deviates from the reference sample by more than a threshold.

3. The method of claim 1, wherein determining whether the metal surface is contaminated based on the IR beam as reflected by the metal surface comprises comparing the IR beam as reflected by the metal surface to a reference sample, and concluding that the metal surface is contaminated when the IR beam as reflected thereby deviates from the reference sample by more than a threshold.

4. The method of claim 1, further comprising repeating impinging the metal surface of the semiconductor die, measuring the IR beam as reflected, and determining whether the metal surface is contaminated as an in-line process for each of a number of additional semiconductor dies.

5. The method of claim 1, wherein the metal surface comprises a bonding pad.

6. A method comprising:
    transferring a semiconductor wafer to a stage;
    for each of a number of semiconductor dies of the semiconductor wafer,
        positioning a metal surface of the semiconductor die under an infrared (IR) probe;
        impinging the metal surface of the semiconductor die with an IR beam by the IR probe, employing an attenuated total reflectance technique;
        measuring the IR beam as reflected by the metal surface by measuring an interferogram of the metal surface, and performing a Fourier transform on the interferogram;
        determining whether the metal surface of the semiconductor die is contaminated based on the IR beam as reflected by the metal surface; and,
    transferring the semiconductor wafer from the stage.

7. The method of claim 6, wherein determining whether the metal surface is contaminated based on the IR beam as reflected by the metal surface comprises comparing the Fourier transform of the interferogram to a reference sample and concluding that the metal surface is contaminated when the Fourier transform of the interferogram deviates from the reference sample by more than a threshold.

8. The method or claim 6, wherein determining whether the metal surface is contaminated based on the IR beam as reflected by the metal surface comprises comparing the IR beam as reflected by the metal surface to a reference sample, and concluding that the metal surface is contaminated when the IR beam as reflected thereby deviates from the reference sample by more than a threshold.

9. The method of claim 6, further comprising repeating the method for each of a number of additional semiconductor wafers.

10. The method of claim 6, wherein the metal surface comprises a bonding pad.

* * * * *